United States Patent [19]

Okada et al.

[11] Patent Number: 5,275,825
[45] Date of Patent: Jan. 4, 1994

[54] COMPRESSED-MOLDED PREPARATIONS

[75] Inventors: Minoru Okada, Inzai; Toshiaki Horie; Hirohisa Okuyama, both of Tomisato; Syuichi Kasai, Narita; Akira Iwasa, Yotsukaido, all of Japan

[73] Assignee: SS Pharmaceutical Co., Ltd., Tokyo, Japan

[21] Appl. No.: 757,983

[22] Filed: Sep. 12, 1991

Related U.S. Application Data

[62] Division of Ser. No. 293,108, Jan. 3, 1989, Pat. No. 5,186,943.

[30] Foreign Application Priority Data

Aug. 22, 1988 [JP] Japan ................ 63-207956
Nov. 11, 1988 [JP] Japan ................ 63-285287

[51] Int. Cl.$^5$ .................... A61K 9/16; A61K 9/26
[52] U.S. Cl. .................... 424/490; 424/494; 424/495; 424/497; 424/498; 424/470
[58] Field of Search .............. 424/490, 494–495, 470, 469

[56] References Cited

U.S. PATENT DOCUMENTS

| | | | |
|---|---|---|---|
| 4,415,547 | 11/1983 | Yu et al. ................... | 424/469 |
| 4,532,562 | 8/1985 | Ikegami et al. ............ | 424/494 X |
| 4,634,587 | 1/1987 | Hsiao ....................... | 424/495 |
| 4,695,467 | 9/1987 | Uemura et al. ............ | 424/502 |
| 4,702,919 | 10/1987 | Kitamori et al. .......... | 424/480 |
| 4,738,848 | 4/1988 | Yoshida et al. ............ | 424/449 |
| 4,748,023 | 5/1988 | Tamás et al. ............. | 424/465 |
| 4,764,378 | 8/1988 | Keith et al. ............... | 424/464 X |
| 4,764,380 | 8/1988 | Urquhart et al. .......... | 424/465 |
| 4,794,001 | 12/1988 | Mehta et al. .............. | 424/458 |
| 4,814,178 | 3/1989 | Bolton et al. ............. | 424/464 X |
| 4,837,031 | 6/1989 | Denton ..................... | 424/464 |
| 4,968,505 | 11/1990 | Okada et al. .............. | 424/498 |

FOREIGN PATENT DOCUMENTS

| | | |
|---|---|---|
| 0052076 | 5/1982 | European Pat. Off. . |
| 0196546 | 10/1986 | European Pat. Off. . |
| 0207041 | 12/1986 | European Pat. Off. . |
| 0257310 | 3/1988 | European Pat. Off. . |
| 2385388 | 10/1978 | France . |
| 0908282 | 10/1962 | United Kingdom . |
| 1358915 | 7/1974 | United Kingdom . |
| 8101652 | 6/1981 | World Int. Prop. O. . |

*Primary Examiner*—Edward Webman
*Attorney, Agent, or Firm*—Oblon, Spivak, McClelland, Maier & Neustadt

[57] ABSTRACT

Compressed molded preparations are disclosed. In the preparation coated granules of a pharmaceutical composition are compressed and molded together with non-coated component(s) containing 10% or more by weight of non-swelling polymers. According to the preparation there is little breakdown of the coating of coated granules at the time of compressing and molding, and the rate of disintegration, and in turn, the release rate of the pharmaceutical component, can be freely controlled or modulated.

5 Claims, No Drawings

COMPRESSED-MOLDED PREPARATIONS

This is a division of application Ser. No. 07/293,108, filed on Jan. 03, 1989 U.S. Pat. No. 5,186,943.

BACKGROUND OF THE INVENTION

1. Field of the Invention

The present invention relates to compressed-molded preparations in which a composition comprising coated granules of a pharmaceutical component is compressed and molded to give a single dosage form. More particularly, the invention relates to compressed-molded preparations in which there is little breakdown of the coating of coated granules at the time of compressing and molding, and also, to preparations in which the rate of disintegration, and in turn, the release rate of the pharmaceutical component, can be freely controlled or modulated.

2. Description of the Background

It is well known that granules coated with coatings possessing water insoluble, intestinally soluble, acid soluble, or water soluble features can be used in order to obtain granules having sustained-release characteristics, or taste- and smell-masking characteristics. However, when the coated granules are processed to form compressed-molded tablet preparations, the coating of the coated granule is very often destroyed by the pressure which is applied, thus damaging the function of the coatings. Since advanced and sophisticated technologies are needed because of this reason, coated granule preparations are usually marketed as they are or in capsule form.

As a means to solve such problems, a method for preparing tablets which involves using microcrystalline cellulose together with the coated granules has been proposed (Japanese Patent Laid-open No. 221115/1986). However, when a large amount of microcrystalline cellulose is used in the non-coated component, the stability of the active components may be lost or damaged, or the manufacturing procedure of the preparation may become difficult, depending upon the form of the non-coated component, or the active drug ingredient or the compound used for producing the coated granules. Also, because the disintegrability of microcrystalline cellulose is high, it is difficult to control the rate of movement of the coated granules in the alimentary canal, as well as the release rate of the active ingredient from the non-coated component.

In view of such a present situation, the inventors carried out research related to compressed-molding of compositions containing coated granules. As a result of the research, it was discovered that by formulating a non-swelling polymer into the non-coated components, compressed-molded preparations could be obtained which were hard enough for practical use, and yet of which coating applied to the coated granules was resistant to destruction. Also, it was found that the disintegration characteristics of the compressed-molded preparations as well as the release charactertics of the active ingredient could be freely controlled or modulated by controlling the amount of non-swelling polymers to be formulated and also by adding disintegrators, waxes, etc. Such findings have led to the completion of the present invention.

SUMMARY OF THE INVENTION

Accordingly, an object of this invention is to provide compressed-molded preparations, in which coated granules of a pharmaceutical composition are compressed and molded together with non-coated component(s) containing 10% or more by weight of non-swelling polymers.

Another object of this invention is to provide said compressed-molded preparations, wherein said coated granules are comprised of the pharmaceutical composition which is coated with a layer of one or more members selected from the group consisting of water insoluble polymers, intestinally soluble polymers, paraffin waxes, higher alcohols, higher fatty acid esters, and higher fatty acids or their salts.

Still another object of this invention is to provide said compressed-molded preparations possessing, on top of said layer of a coated material, a protective coating layer of a water soluble polymer or an acid soluble polymer.

One more object of this invention is to provide compressed-molded preparations, wherein said coated granules are comprised of a pharmaceutical composition (comprising diclofenac sodium and an organic acid) on which a sustained-release coating is coated.

Other objects, features and advantages of the invention will hereinafter become more readily apparent from the following description.

DETAILED DESCRIPTION OF THE INVENTION AND PREFERRED EMBODIMENTS

In the present invention, the coated granule can be any pharmaceutical composition which is produced by conventional granulation methods, inasmuch as the same contains an active ingredient and possesses a coating.

There is no particular limitation or restriction as to the compound used as the coating. Specific examples which can be given include water insoluble polymers such as ethylcellulose, aminoalkyl methacrylate copolymer, polyvinyl acetate, polyvinyl chloride, polyethylene, and the like; intestinally soluble polymers such as cellulose acetate phthalate, hydroxypropyl methyl cellulose phthalate, hydroxypropyl methylcellulose acetate succinate, carboxymethylethylcellulose, styrene-acrylic acid copolymer, methacrylic acid copolymer, maleic anhydride copolymer, shellac, and the like; paraffin waxes such as paraffin, microcrystalline wax, and the like; higher alcohols such as stearyl alcohol, cetyl alcohol, and the like; higher fatty acid esters such as glycerine esters of fatty acid, hydrogenated oils, carnauba wax, beeswax, Japan (haze) wax, and the like; higher fatty acids such as stearic acid, palmitic acid, myristic acid, behenic acid, and the like (or the sodium, calcium or magnesium salts of these higher fatty acids), acid soluble polymers such as polyvinylacetal diethylaminoacetate, aminoalkyl methacrylate copolymer E, and the like; and water soluble polymers such as hydroxypropyl methylcellulose, methylcellulose, hydroxypropyl cellulose, polyvinyl pyrrolidone, polyethylene glycol, gelatin, and the like. These compounds can be used alone or in combinations of two or more.

Also, coated granules with a primary coating layer comprising one or more types of compounds amoung from water insoluble polymers, intestinally soluble polymers, paraffin waxes, higher alcohols, fatty acid esters, and higher fatty acid or their salts, on the pharmaceutical composition, and further with a protective coating on top of this primary coating layer which is comprised of water soluble or acid soluble polymers, can provide even greater protection against destruction of the coating at the time of compressing-molding.

Here, the same compounds as mentioned previously are used as the coating for the primary coating and the protective coating.

A pharmaceutical composition which comprises diclofenac sodium as an active ingredient together with an organic acid, if applied a sustained-release coating to form coated granules, can be made into a long-lasting preparation which gives a decreased maximum plasma diclofenac concentration, causes decreased side effects, and yet maintains a constant plasma diclofenac concentration for a prolonged time.

There is no particular limitation or restriction on the organic acids which can be used. Specific examples which can be given include citric acid, ascorbic acid, fumaric acid, tartaric acid, succinic acid, malic acid, and adipic acid, as well as mixtures of any of these compounds. It is desirable to formulate 2 parts or more by weight of organic acid to 100 parts by weight of diclofenac sodium.

As the sustained-release coating, the previously mentioned water insoluble polymers, intestinally soluble polymers, paraffin waxes, higher alcohols, higher fatty acid esters, higher fatty acids or their salts, and the like, can be given as examples. These compounds can be used alone or in combinations of two or more.

The coated granules are produced by various methods. One method involves granulating the pharmaceutical composition by a conventional method and then applying a coating to the granules. Another involves producing coated granules by methods such as microencapsulation of the pharmaceutical composition.

The amounts of coating materials differ depending upon the type of the coated materials. Normally, it accounts for 1 to 80%, on a weight basis, of the pharmaceutical composition, with 3 to 60% being the most desirable.

The compressed-molded preparations of the present invention can be prepared using non-coated components containing the non-swelling polymers as is, or after processing such components into powder for tablet use by using dry or wet granulation methods. Such non-coated components or the powders are then mixed with the granules of coating material and molded by any of known compression-molding methods.

The desirable non-swelling polymers for use here are those possessing a high degree of compressability/moldability, as well as a low degree of disintegration characteristic. Specific examples which can be given include water insoluble polymers such as ethylcellulose, aminoalkyl methacrylate copolymer, polyvinyl acetate, polyvinyl chloride, polyethylene, and the like; intestinally soluble polymers such as cellulose acetate phthalate, hydroxypropyl methylcellulose phthalate, hydroxypropyl methylcellulose acetate succinate, carboxymethylethylcellulose, styreneacrylic copolymer, methacrylic acid copolymer, maleic anhydride copolymer, and the like; acid soluble polymers such as polyvinylacetal diethylamino acetate, aminoalkyl methacrylate copolymer E, and the like; and water soluble polymers such as hydroxypropyl methylcellulose, methylcellulose, hydroxypropyl cellulose, polyvinylpyrrolidone, and the like. These compounds can be used alone or in combinations of two or more.

In order to prevent the destruction of the coating of the coated granules and to control or modulate the disintegration characteristics of the coating, the amount of the non-swelling polymers to be formulated must be greater than 10% by weight of the amount of the non-coated components. It is possible to formulate the active ingredient into these non-coated components. In particular, when the drug ingredient is diclofenac sodium, a preparation having an excellent prolonged effect can be obtained, if the percentage of non-coated diclofenac sodium added to the non-coated components is between 10 and 50%, especially 20 to 40%, on a weight basis, of the total amount of diclofenac sodium.

To the compressed-molded preparation of the present invention, appropriate, well known substances, such as vehicles, binders, disintegrators, disintegration retarding agents, lubricants, coloring agents, flavoring substances, stabilizers, and the like can be formulated as desired.

The compressed-molded preparation obtained in this way can also be processed into a film-coated tablet, a sugar-coated tablet, a press-coated tablet, or a multi-layered tablet.

The compressed-molded preparation thus prepared according to the present invention, when combined with the special characteristics of the coating granule, or also, with the special characteristics of the active ingredient, can be used as a single dosage form which is hard enough for practical use, without impairing the function of the coating of the coated granule. In addition, the release rate of the active component from the non-coated component, as well as the disintegration time of the compressed-molded preparation, can be controlled or modulated.

Therefore, the preparations are easier to administer and can impart a more prolonged drug effect than sustained-release preparations using coated granules alone.

Other features of the invention will become apparent in the course of the following description of the exemplary embodiments which are given for illustration of the invention and are not intended to be limiting thereof.

EXAMPLES

Example 1

1) Preparation of Non-coated Granules (a):

800 g of diclofenac sodium was mixed with 280 g of corn starch and pulverized, resulting in fine powders. These fine powders were processed to produce spherical granules, using 720 g of purified sucrose that had been obtained by shifting through 20–28 mesh as a core, while pouring a solution of hydroxypropyl cellulose (25 g) which had been dissolved in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules (a).

2) Preparation of Coated Granules (b):

Coated granules (b) were produced according to a conventional spray coating method as follows: 600 g of non-coated granules (a) produced in 1) above was placed into a fluid-type coating apparatus, followed by sparay coating using 1263 g of the coating liquid having the composition listed below. The weight of the coating with respect to the weight of the non-coated granule was 8%.

| Composition of Coating Liquid | % |
| --- | --- |
| Ethylcellulose | 2.7 |
| Polyvinylpyrrolidone K-30 | 0.9 |
| Talc | 0.2 |
| Ethyl alcohol | 96.2 |
| Total | 100.0 |

Example 2

Preparation of Coated Granule (c):

Coated granules (c) were produced according to a conventional spray coating method as follows: 600 g of non-coated granule (a) obtained in Example 1 was placed into a fluid-type coating apparatus, followed by spray coating using 1667 g of the coating liquid having the composition listed below. The weight of the coating with respect to the weight of the non-coated granules was 20%.

| Composition of Coating Liquid | % |
| --- | --- |
| Aminoalkyl methacrylate copolymer L | 6.5 |
| Glycerin ester of fatty acid | 0.5 |
| Talc | 0.2 |
| Ethyl alcohol | 92.8 |
| Total | 100.0 |

Example 3 i) Preparation of Compressed-Molded Preparation (d-1):

500 g of the non-coated granules (a) produced in 1), Example 1, was placed in a small coating pan. The pan was rotated at 35 rpm while sending hot air through at 90° C. 40 g of hydrogenated castor oil was poured and when the hydrogenated oil began to melt, 80 g of magnesium stearate was added in five 16 g portions to make it adhered onto the granules. In the same way, 40 g of hydrogenated castor oil was poured and 80 g of magnesium magnesium stearate were added in five 16 g portions to make it adhered onto the granules. The same operation was repeated again to produce coated granules (d-1). The weight of the coating with respect to the weight of the non-coated granule was 72%.

ii) Preparation of Compressed-molded Preparation (d-2)

294.3 g of the coated granules produced in 1) above, 263.7 g of ethylcellulose, 30 g of carboxymethylcellulose calcium, 6 g of light anhydrous silicic acid, 3 g of magnesium stearate, and 3 g of talc were uniformly mixed, and then compressed and molded to produce compressed molded tablets (d-2) of the present invention, each tablet having a weight of 300 mg and a diameter of 9 mm.

Example 4

Preparation of Compressed-Molded Preparation (e):

246.3 g of coated granules (b) produced in 2) of Example 1, 300 g of ethylcellulose, 11.7 g of lactose, 30 g of carboxymethylcellulose calcium, 6 g of light anhydrous silicic acid, 3 g of magnesium stearate, and 3 g of talc were uniformly mixed and then compressed and molded. The compress-molded tablet (e) of the present invention thus obtained each weighed 300 mg and had a diameter of 9 mm.

Test Example 1

The dissolution of active ingredient from compressed-molded preparation (e) obtained in Example 4 and coated granules (b) obtained in 2) of Example 1 were measured by the rotating paddle method (Japan Pharmacopeia—11th Edition) using a pH 6.8 buffer as a test solution. The results are shown in Table 1. It was found that there were almost no changes in the dissolution of active ingredient from coating granule (b) (prior to compression and molding) and the present invention compressed-molded preparation (e) (after compression-molding).

TABLE 1

| Time (hr) | Dissolution (%) | |
| --- | --- | --- |
| | Example 4 | 2) of Example 1 |
| 1 | 40.2 | 38.7 |
| 3 | 82.9 | 79.2 |

Example 5 i) Preparation of Compressed-Molded Preparation (f-1):

70 g of an aqueous solution of hydroxypropyl cellulose (10% w/w) was added to a powder mixture consisting of 300 g of ethylcellulose, 118 g of lactose, and 25 g of corn starch. The mixture was then kneaded and granules were produced according to a conventional method. Next, 253.55 g of the resulting granules, 68.45 g of coated granules (c) from Example 2, 20 g of carboxymethylcellulose calcium, 4 g of light anhydrous silicic acid, 2 g of magnesium stearate, and 2 g of talc were uniformely blended, and compressed and molded. The resulting tablets, compressed-molded preparation (f-1) of the present invention, each weighed 350 mg and had a diameter of 9 mm.

ii) Preparation of Compressed-Molded Preparation (f-2):

70 g of an aqueous solution of hydroxypropyl cellulose (10% w/w) was added to a powder mixture consisting of 200 g of ethylcellulose, 218 g of lactose, and 25 g of corn starch. The mixture was then kneaded and granules were produced according to a conventional method. Next, 253.55 g of the resulting granules were uniformly mixed with 68.45 g of coated granules (c) from Example 2, 20 g of carboxymethylcellulose calcium, 4 g of light anhydrous salicic acid, 2 g of magnesium stearate, and 2 g of talc. The mixture was then compressed and molded. The resulting tablets, compressed-molded preparation (f-2) of the present invention, each weighed 350 mg and had a diameter of 9 mm.

iii) Preparation of Compressed-Molded Preparation (f-3):

70 g of an aqueous solution of hydroxypropyl cellulose (10% w/w) was added to a powder mixture consisting of 100 g of ethylcellulose, 318 g of lactose, and 25 g of corn starch. The mixture was then kneaded and granules were produced according to a conventional method. Next, 253.55 g of the granules obtained was uniformly mixed with 68.45 g of coated granules (c) from Example 2, 20 g of carboxymethylcellulose calcium, 4 g of light anhydrous silicic acid, 2 g of magnesium stearate, and 2 g of talc. The mixture was then compressed and molded to obtain tablets, the compressed-molded preparation (f-3) of the present invention, each weighing 350 mg and having a diameter of 9 mm.

Comparative Example 1

Preparation of Regular Compressed-Molded Preparation (g):

70 g of an aqueous solution of hydroxypropyl cellulose (10% w/w) was added to a powder mixture consisting of 200 g of mannitol, 218 g of lactose, and 25 g of corn starch. The mixture was then kneaded and granules were produced according to a conventional method. Next, 253.55 g of the granules obtained was mixed together with 68.45 g of coated granules (c) from Example 2, 20 g of carboxymethylcellulose calcium, 4 g of light anhydrous silicic acid, 2 g of magnesium stearate, and 2 g of talc. The mixture was then uniformly blended and compressed and molded. The resulting tablets each weighed 350 mg and had a diameter of 9 mm. These tablets were taken as regular compressed-molded preparation (g).

Test Example 2

The dissolution of active ingredient from compressed-molded preparations (f-1), (f-2), and (f-3) from Example 5 and compressed-molded preparation (g) obtained from Comparative Example 1 were measured by the rotating paddle method (Japan Pharmacopeia, 11th Edition) using a pH 4.5 buffer as a test solution. The results are shown in Table 2. Compared to compressed-molded preparation (g), the effectiveness of the compressed-molded preparations in ethylcellulose of the present invention was clear. Also, as the percentage of ethylcellulose in the non-coated component was increased, destruction of the coating of the coated granule could be prevented.

TABLE 2

| Time (min) | Dissolution (%) | | | |
|---|---|---|---|---|
| | (f-1) | (f-2) | (f-3) | Regular compressed-molded preparation (g) |
| 30 | 2.8 | 4.7 | 8.5 | 52.6 |

Example 6 i) Preparation of Compressed-Molded Preparation (h-1):

80 g of an aqueous solution of hydroxypropyl cellulose (10% w/w) were added to a powder mixture consisting of 23.3 g of diclofenac sodium, 240 g of ethyl cellulose, 153.7 g of lactose, and 25 g of corn starch. The mixture was then kneaded and granules were produced according to a conventional method. Next, 241.55 g of the granules obtained were mixed with 68.45 g of coated granules (c) from Example 2, 32 g of ethylcellulose, 4 g of light anhydrous silicic acid, 2 g of magnesium stearate, and 2 g of talc. The mixture was uniformly blended and then compressed and molded. Each of the resulting tablets weighed 350 mg and had a diameter of 9 mm. These tablets were taken as compressed-molded preparation (h-1) of the present invention.

ii) Preparation of Compressed-Molded Preparation (h-2):

80 g of an aqueous solution of hydroxypropyl cellulose (10% w/w) was added to a powder mixture consisting of 23.3 g of diclofenac sodium, 240 g of ethylcellulose, 153.7 g of lactose, and 25 g of corn starch. The mixture was then kneaded and granules were produced according to a conventional method. Next, 241.55 g of the granules obtained was mixed with 68.45 g of coated granules (c) from Example 2, 22 g of ethylcellulose, 10 g of carboxymethyl-cellulose, 4 g of light anhydrous silicic acid, 2 g of magnesium stearate, and 2 g of talc. The mixture was uniformly blended and then compressed and molded. Each of the resulting tablets weighed 350 mg and had a diameter of 9 mm. These tablets were taken as compressed-molded preparation (h-2) of the present invention.

iii) Preparation of Compressed-Molded Preparation (h-3):

80 g of an aqueous solution of hydroxypropyl cellulose (10% w/w) was added to a powder mixture consisting of 23.3 g of diclofenac sodium, 240 g of ethylcellulose, 153.7 g of lactose, and 25 g of corn starch. The mixture was then kneaded and granules were produced according to a conventional method. Next, 241.55 g of the granules, obtained was mixed with 68.45 g of coated granules (c) from Example 2, 8 g of ethyl cellulose, 24 g of carboxymethyl-cellulose calcium, 4 g of light anhydrous silicic acid, 2 g of magnesium stearate, and 2 g of talc. The mixture was uniformly blended and then compressed and molded. Each of the resulting tablets weighed 350 mg and had a diameter of 9 mm. These tablets were taken as compressed-molded preparation (h-3) of the present invention.

Comparative Example 2

Preparation of Regular Compressed-Molded Preparation (i):

80 g of an ethyl alcohol solution of hydroxypropyl cellulose (10% w/w) was added to a powder mixture consisting of 20.6 g of diclofenac sodium, 240 g of microcrystalline cellulose, 156.4 g of lactose and 25 g of corn starch. The mixture was then kneaded and granules were produced according to a conventional method. Next, 273.55 g of the granules obtained was mixed with 68.45 g of coated granules (c) from Example 2, 4 g of light anhydrous silicic acid, 2 g of magnesium stearate, and 2 g of talc. The mixture was uniformly blended and then molded and compressed. Each of the resulting tablets weighed 350 mg and had a diameter of 9 mm. These tablets were taken as regular compressed-molded preparations (i).

Test Example 3

The dissolution of active ingredient from compressed-molded preparations (h-1), (h-2) and (h-3) obtained from Example 6 and compressed-molded preparation (i) obtained from Comparative Example 2 were measured by the rotating paddle method (Japan Pharmacopeia, 11th Edition) using a pH 4.5 buffer as a test solution. The results are shown in Table 3. It was found that the elution rate of the rapid dissolving portion of the compressed-molded preparation of the present invention could be controlled or modulated, however, for regular compressed-molded preparation (i), it was difficult to control or modulate the dissolution of active ingredient from the rapid dissolving portion.

TABLE 3

| Time (min) | Dissolution (%) | | | |
|---|---|---|---|---|
| | (h-1) | (h-2) | (h-3) | Regular compressed-molded preparation (i) |
| 30 | 9.1 | 25.6 | 37.5 | 34.5 |
| 60 | 18.6 | 37.8 | 38.1 | 35.2 |

Test Example 4

The disintegration test (Japan Pharmacopeia, 11th Edition) using water as the test fluid was carried out on compressed-molded preparations (h-1), (h-2) and (h-3) obtained from Example 6 and compressed-molded preparation (i) obtained from Comparative Test 2. The results are shown in Table 4. It was found that the disintegration times of the compressed-molded preparations of the present invention were controlled.

TABLE 4

| | Disintegration Time (min) | | |
|---|---|---|---|
| (h-1) | (h-2) | (h-3) | Regular compressed-molded preparation (i) |
| 92 | 32 | 3 | 2 |

Example 7

800 g of theophylline and 400 g of corn starch were mixed and pulverized, resulting in fine powders. These fine powders were processed to produce spherical granules, using 600 g of purified sucrose that had been obtained by shifting through 28–35 mesh as a core, while pouring a solution of hydroxypropyl cellulose (25 g) which had been dissolved in 475 g of ethyl alcohol. The granules were then dried for 3 hours at 55° C. Non-coated granules (j) were taken as those dried granules which would pass through a 16 mesh but not a 32 mesh. Coated granules (k) were produced by a conventional spray coating method as follows: 600 g of non-coated granules (j) was placed into a fluid-type coating apparatus, followed by spray-coating using 1263 g of the coating fluid having a composition presented below. The weight of this coating with respect to the weight of the non-coated granules was 8%.

| Composition of Coating Liquid | % |
|---|---|
| Ethylcellulose | 2.4 |
| Polyvinylpyrrolidone K-30 | 1.2 |
| Talc | 0.2 |
| Ethyl alcohol | 96.2 |
| Total | 100.0 |

246.3 g of coated granules (k), 300 g of ethylcellulose, 41.7 g of lactose, 6 g of light anhydrous silicic acid, 3 g of magnesium stearate, and 3 g of talc were uniformly mixed, followed by compressing and molding. Each tablet weighed 300 mg and had a diameter of 9 mm. These tablets were taken as compressed-molded preparation (l).

Example 8

800 g of indomethacin and 400 g of corn starch were mixed and pulverized, resulting in fine powders. These fine powders were processed to produce spherical granules, using 600 g of purified sucrose that had been obtained by shifting through 28–35 mesh as a core, while pouring a liquid consisting of 25 g of hydroxypropyl cellulose dissolved in 475 g of ethyl alcohol. The granules were dried for 3 hours at 55° C. Non-coated granules (m) were taken as those granules which would pass through a 16 mesh but not a 32 mesh. Coated granules (n) were produced by a conventional spray coating method as follows: 600 g of non-coated granules (m) was placed into a fluid-type coating apparatus, followed by spray-coating using 1263 g of the coating liquid having a composition presented below. The weight of this coating with respect to the weight of the non-coated granules was 8%.

| Composition of Coating Liquid | % |
|---|---|
| Ethylcellulose | 3.0 |
| Polyvinylpyrrolidone K-30 | 0.6 |
| Talc | 0.2 |
| Ethyl alcohol | 96.2 |
| Total | 100.0 |

246.3 g of coated granule (n), 50 g of indomethacin, 250 g of ethyl cellulose, 41.7 g of lactose, 6 g of light anhydrous silicic acid, 3 g of magnesium stearate, and 3 g of talc were uniformly mixed and then compressed and molded. Each of the resulting tablets weighed 300 mg and had a diameter of 9 mm. These tablets were taken as compressed-molded preparation (o) of the present invention.

Example 9

1) Preparation of Non-coated Granule (p):

525 g of diclofenac sodium and 285 g of corn starch were mixed and pulverized, resulting in fine powders. These fine powders were processed to produce spherical granules, using 420 g of purified sucrose that had been obtained by shifting through 24–28 mesh as a core, while pouring a liquid consisting of 25.2 g of hydroxypropyl cellulose dissolved in 478.8 g of ethyl alcohol. The granules were dried for 3 hours at 55° C. Non-coated granules (p) were taken as those dried granules which passed through 14 mesh but not 32 mesh.

2) Preparation of Primary Coated Granule (q):

Primary coated granules (q) were produced by placing 1000 g of non-coated granule (p) into a fluid-type coating apparatus, followed by spray coating using 3472 g of the coating fluid having a composition below according to a conventional method. The weight of this coating with respect to the weight of the non-coated granule was 25%.

| Composition of Coating Liquid | % |
|---|---|
| Dimethyl methacrylate copolymer-S | 6.5 |
| Glycerin ester of fatty acid | 0.5 |
| Talc | 0.2 |
| Ethyl alcohol | 92.8 |
| Total | 100.0 |

3) Preparation of Granule (r) Possessing a Protective Coating:

Granule (r) possessing a protective coating was produced according to a conventional spray coating method as follows: 600 g of primary coated granule (q) was placed into a fluid-type coating apparatus, followed by spray-coating using 1667 g of the coating liquid having a composition shown below. The weight of this coating with respect to the weight of the primary coating (q) was 20%.

| Composition of Coating Liquid | % |
|---|---|
| Hydroxypropyl methylcellulose | 6.5 |
| Macrogol 6000 | 0.5 |
| Talc | 0.2 |
| Ethyl alcohol | 66.8 |
| Purified water | 26.0 |

| Composition of Coating Liquid | % |
| --- | --- |
| Total | 100.0 |

4) Preparation of Compressed-Molded Preparation (s):

512 g of an aqueous solution of hydroxypropyl cellulose (10% w/w) was added to a powder mixture consisting of 45 g of diclofenac sodium, 694.8 g of ethylcellulose, 90 g of lactose, 42.4 g of corn starch, 79.6 g of croscarmellose sodium type-A, and 118.8 g of low-substituted hydroxypropyl cellulose. The mixture was then kneaded and granules were produced according to a conventional method. Next, 560.9 g of the granules obtained was mixed with 188.28 g of granule (r) possessing the protective coating, 34.82 g of microcrystalline cellulose, 8 g of light anhydrous silicic acid, 4 g of magnesium stearate, and 4 g of talc. The mixture was uniformly blended and compressed and molded. The resulting tablets each weighed 200 mg and had a diameter of 8 mm. These tablets were taken as compressed-molded preparation (s) of the present invention.

Test Example 5

The dissolution of active ingredient from compressed-molded preparation (s) of the present invention obtained in Example 9 and that of the fine powders for tablet used prior to compression-molding were measured by the rotating paddle method (Japan Pharmacopeia, 11th Edition) using a pH 4.5 buffer as a test solution. The results are shown in Table 5. It was found that there were no changes in the dissolution of active ingredient from the compressed-molded preparation of the present invention before or after compression-molding.

TABLE 5

| Time (min) | Dissolution (%) | |
| --- | --- | --- |
| | (s) | fine powders for tablet use for (s) |
| 30 | 33.1 | 32.1 |

Example 10

1) Preparation of Non-coated Granules (t):

525 g of diclofenac sodium, 130 g of fumaric acid, 55 g of talc, and 10 g of corn starch were mixed and pulverized to form fine powders. These fine powders were processed to produce spherical granules, using 480 g of purified sucrose that had been obtained by shifting through 24-28 mesh as a core, while pouring a liquid consisting of 27 g of hydroxypropyl cellulose dissolved in 513 g of ethyl alcohol. The granules were dried for 3 hours at 55° C. Non-coated granules (t) were taken as the dried granules which passed through 14 mesh but not 32 mesh.

2) Preparation of Coated Granules (u):

Coated granules (u) were produced according to a conventional spray coating method as follows: 600 g of non-coated granules (t) was placed into a fluid-type coating apparatus followed by spray-coating using 2083 g of the coating liquid having a composition shown below. The weight of this coating with respect to the weight of the non-coated granule was 25%.

| Composition of Coating Liquid | % |
| --- | --- |
| Aminoalkyl methacrylate opolymer S | 6.5 |
| Glycerin ester of fatty acid | 0.5 |
| Talc | 0.2 |
| Ethyl alcohol | 92.8 |
| Total | 100.0 |

3) Preparation of Compressed-Molded Preparation (v):

240 g of an aqueous solution of 10% hydroxypropyl methylcellulose were added to a powder mixture consisting of 45 g of diclofenac sodium, 500 g of ethylcellulose, 119 g of lactose, 40 g of corn starch, and 24 g of croscarmellose sodium Type A. The mixture was then kneaded and granules were produced by a conventional method. Next, 188 g of the granules obtained were mixed with 76.7 g of coated granule (u), 29.3 g of ethylcellulose, 3 g of light anhydrous silicic acid, 1.5 g of magnesium stearate, and 1.5 g of talc. The mixture was uniformly blended and then compressed and molded. The resulting tablets each weighed 300 mg and had a diameter of 9 mm. These tablets were taken as compressed-molded preparation (v) of the present invention.

Example 11

1) Preparation of Non-coated Granule (w):

525 g of diclofenac sodium, 55 g of talc, and 140 g of corn starch were mixed and pulverized, resulting in fine powders. These fine powders were processed to produce spherical granules, using 480 g of purified sucrose that had been obtained by shifting through 24-28 mesh as a core, while pouring a liquid consisting of 27 g of hydroxypropyl cellulose dissolved in 513 g of ethyl alcohol. The granules were dried for 3 hours at 55° C. Non-coated granules (w) were taken as the dried granules which passed through 14 mesh but not 32 mesh.

2) Preparation of Coated Granule (x):

Coated granules (x) were produced according to a conventional spray coating method as follows: 600 g of non-coated granule (w) was placed into a fluid-type coating apparatus followed by spray coating using 2083 g of the coating liquid having a composition shown below. The weight of the coating with respect to the weight of the non-coated granule was 25%.

| Composition of the Coating Liquid | % |
| --- | --- |
| Aminoalkyl methacrylate copolymer-S | 6.5 |
| Glycerin ester of fatty acid | 0.5 |
| Talc | 0.2 |
| Ethyl alcohol | 92.8 |
| Total | 100.0 |

3) Preparation of Compressed-Molded Preparation (y):

240 g of an aqueous solution of hydroxypropyl cellulose were added to a powder mixture consisting of 45 g of diclofenac sodium, 500 g of ethylcellulose, 119 g of lactose, 40 g of corn starch and 24 g of croscarmellose sodium Type A. The mixture was then kneaded and granules were produced according to a conventional method. Next, 376 g of the granules obtained, 153.4 g of coated granules (x), 58.6 g of ethyl cellulose, 6 g of light anhydrous silicic acid, 3 g of magnesium stearate, and 3 g of talc were uniformly mixed and then compressed and molded to produce tablets. The weight of each tablet was 300 mg and the diameter was 9 mm. These tablets were taken as compressed-molded preparation (y) of the present invention.

Test Example 6

The dissolution of active ingredient from compressed-molded preparations (v) obtained from Example 10 and (y) obtained from Example 11, as well as their respective fine powders for use for tablets, were measured by the rotating paddle method (Japan Pharmacopeia, 11th Edition). A pH of 4.5 buffer test solution was used from the beginning of the test until 30 min, while after that a pH of 7.5 buffer test solution was used. The results are shown in Table 7. No changes in the dissolutions of active ingredient were observed for the compressed-molded preparations of the present invention between before and after compression-molding. Also, active ingredient of the compressed-molded preparation (v), which contained organic acids, was more slowly released than that of compressed-molded preparation (y) which did not contain organic acids.

TABLE 7

| Time (min) | Dissolution (%) | | | |
|---|---|---|---|---|
| | (v) | (v) fine powders | (y) | (y) fine powders |
| 30 (pH 4.5) | 29.5 | 30.8 | 32.3 | 30.2 |
| 60 (pH 7.5) | 68.4 | 67.7 | 98.2 | 98.6 |
| 90 (pH 7.5) | 95.6 | 94.8 | 99.5 | 99.4 |

Example 12

1) Preparation of Double-layered Granules (z):

Double-layer coated granules (z) were produced according to a conventional spray coating method as follows; 600 g of the coated granules (u) from 2) of Example 10 were placed into a fluid-type coating apparatus followed by spray coating using 1667 g of the coating liquid having a composition shown below. The weight of the coating with respect to the weight of coated granules (u) was 20%.

| Composition of Coating Liquid | % |
|---|---|
| Hydroxypropyl methylcellulose | 6.5 |
| Macrogol 6000 | 0.5 |
| Talc | 0.2 |
| Ethyl alcohol | 66.8 |
| Purified water | 26.0 |
| Total | 100.0 |

2) Preparation of Compressed-Molded Preparation (A):

240 g of an aqueous solution of hydroxypropyl cellulose (10% w/w) were added to a powder mixture consisting of 45 g of diclofenac sodium, 500 g of ethylcellulose, 119 g of lactose, 40 g of corn starch, and 24 g of A-type croscarmellose sodium Type A. The mixture was kneaded and then granules were produced according to a conventional method. Next, 376 g of the granules obtained was mixed with 184.1 g of double-layer coated granules (z), 27.9 g of microcrystalline cellulose, 6 g of light anhydrous silicic acid, 3 g of magnesium stearate and 3 g of talc. After uniformly blending the mixture, compression and molding were carried out. The weight of the tablets was 300 mg and the diameter 9 mm. These tablets were taken as compressed-molded preparation (A) of the present invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent is:

1. A compressed-molded preparation consisting essentially of:
   a) coated granules of a pharmaceutical composition comprising a pharmaceutically active component in the core;
   b) a non-coated component consisting essentially of 10% or more by weight of a non-swelling polymer selected from the group consisting of ethyl cellulose, amino alkyl methacrylate copolymer, polyvinyl acetate, polyvinyl chloride, polyethylene, cellulose acetate phthalate, hydroxypropyl methylcellulose phthalate, hydroxypropyl methylcellulose acetate succinate, carboxymethyl ethylcellulose, styrene-acrylic acid copolymer, methacrylic acid copolymer, maleic anhydride copolymer, polyvinylacetal diethylamine acetate, aminoalkyl methacrylate copolymer E, hydroxypropyl methylcellulose, methylcellulose, hydroxypropyl cellulose, polyvinylpyrrolidone, and mixtures thereof;
   wherein said coated granules are compressed and molded together with said non-coated component.

2. The compressed-molded preparation of claim 1, wherein the coating of said coated granules is one member selected from the group consisting of water insoluble polymers, intestinally soluble polymers, paraffin waxes, higher alcohols, higher fatty acid esters, higher fatty acids, salts of higher fatty acids, acid soluble polymers, water soluble polymers, and mixtures thereof.

3. The compressed-molded preparation of claim 1, wherein said core of said coated granules comprises diclofenac sodium as said pharmaceutically active component and a pharmaceutically acceptable organic acid, and the coating of said coated granules is a sustained-release coating.

4. The compressed-molded preparation of claim 3, wherein said sustained-release coating comprises one member selected form the group consisting of water insoluble polymers, intestinally soluble polymers, paraffin waxes, higher alcohols, higher fatty acid esters, higher fatty acids, salts of higher fatty acids and mixtures thereof.

5. The compressed-molded preparation according to claim 1, wherein said non-coated component consists essentially of non-swelling polymers and the pharmaceutically active component.

* * * * *